United States Patent [19]
O'Lenick, Jr.

[11] Patent Number: 5,045,586
[45] Date of Patent: Sep. 3, 1991

[54] LUBRICANTS FOR THERMOPLASTIC RESINS

[76] Inventor: Anthony J. O'Lenick, Jr., 743 Ridgeview Dr., Lilburn, Ga. 30247

[21] Appl. No.: 345,853

[22] Filed: May 1, 1989

Related U.S. Application Data

[63] Continuation-in-part of Ser. No. 228,214, Aug. 4, 1988, abandoned.

[51] Int. Cl.$^5$ .................... C08F 5/08; C08K 5/11
[52] U.S. Cl. ..................... 524/291; 524/310; 524/611; 524/285; 560/56; 560/60; 560/181; 560/182; 560/183; 560/198; 560/199; 560/201; 260/410.6
[58] Field of Search ............... 560/56, 60, 181, 182, 560/183, 198, 199, 201; 260/410.6; 524/291, 310, 285

[56] References Cited

U.S. PATENT DOCUMENTS

| | | | |
|---|---|---|---|
| 3,773,668 | 11/1973 | Denis et al. | 560/198 |
| 4,143,024 | 3/1979 | Adelmann et al. | 524/291 |
| 4,868,236 | 8/1989 | O'Lenick | 560/182 |

*Primary Examiner*—Lewis T. Jacobs

[57] ABSTRACT

The present invention is directed to branched polyesters derived from the reaction product of hydroxy stearic acid or hydroxy stearic alkoxylate, a guerbet alcohol or guerbet alcohol alkoxylate, which product is further reacted with a polycarboxylic acid to provide the required branching in the polyester structure. The invention is also directed to the preparation, compositions and application of said internal plastic lubricants, particularly suited for use in forming of polycarbonate thermoplastics.

20 Claims, No Drawings

LUBRICANTS FOR THERMOPLASTIC RESINS

This is a continuation-in-part of application Ser. No. 228,214, filed Aug. 4, 1988, now abandoned.

The present invention is directed to branched polyesters derived from the reaction product of hydroxy stearic acid or hydroxy stearic alkoxylate, a guerbet alcohol or guerbet alcohol alkoxylate, which product is further reacted with a polycarboxylic acid to provide the required branching in the polyester structure. The invention is also directed to the preparation, compositions and use of said internal plastic lubricants, particularly suited for the forming of polycarbonate thermoplastics.

DISCUSSION OF THE PRIOR ART

There are two different types of plastic lubricants. The mode of action and consequently the application in which each type would be used differ considerably. External lubricants are insoluble in the polymer melt and as such have a tendency to form a mono-layer on the surface of the polymer. This results in decreasing the friction between the polymer surface and the molding element. Such lubricants are referred to as mold release agents. Internal lubricants, on the other hand, are soluble in the polymer melt and as such promote flow of the polymer. These materials promote flow by reduction of internal stress and promotion of intermolecular slippage.

In order to have external lubricant properties, the ester must be able to migrate to the surface of the plastic; thus, lower molecular weight compounds are generally employed. However, blends of internal and external lubricants can result in synergistic interactions and particular improvements in plastic processing. Such blending with the ability to modify the polarity and hydrophobicity of the compounds permit the manufacture of custom lubricants tailor made to satisfy certain specific requirements in the forming of particular plastic materials and affords considerable latitude in formulations prior to molding.

Of the moldable thermoplastics, polycarbonates possess a relatively high viscosity and require higher processing temperatures. The use of internal lubricants for polycarbonate thermoplastics is particularly important in extrusion applications and in high performance injection molding which includes the rapidly expanding field of laser read compact recording discs. A superior grade of polycarbonate has been developed for this application; however, the presence of a mold release agent on the surface of the plastic is found to have a detrimental effect upon performance.

Internal lubrication for polycarbonates is also important for the precision extrusion of polycarbonate sheets where sheet tolerances are an important factor, as in materials of construction for greenhouses. Additionally, polycarbonates used to contain comestible products and beverages must also be free of compounds which migrate to the surface and cause contamination of the product contained therein.

U.S. Pat. No. 4,425,458 discloses diesters containing from 16 to 40 carbon atoms in the alcohol moiety. According to the patent, alcohols of this type are reacted with diacids containing less than 10 carbon atoms to produce the corresponding diester and to obtain insolubility of the resulting lubricant in the polycarbonate product. However, it is found that patentees products are suitable only as mold release agents since their insolubility causes migration to the surface of the plastic upon molding.

Accordingly, it is an object of this invention to provide an internal lubricant which overcomes all of the above shortcomings and which is soluble in the thermoplastic so as to avoid any tendency toward surface migration.

Another object of this invention is to provide an internal lubricant which is capable of being blended with external lubricants so as to incorporate the beneficial lubricating properties of both for certain applications.

Another object of this invention is to provide an economical and commercially feasible process for the preparation of the present products.

Still another object is to provide compositions of polycarbonate thermoplastics and the present internal lubricant useful in the precision forming of polycarbonate sheets and containers for comestible and beverage products.

Yet another object is to provide a polycarbonate composition suitable for the manufacture of laser read compact recording discs.

Yet another object is to provide a high molecular weight ester which has low volatility in a thermoplastic melt and resists plating out on processing equipment.

These and other objects of the invention will become apparent from the following description and disclosure.

THE INVENTION

According to this invention there is provided an lubricating agent having the structure $$[C_6H_{13}-\underset{\underset{\underset{O}{\parallel}}{(CH_2)_{10}C}}{\overset{\overset{R^3}{|}}{CH}}-O-(CH_2CHO)_d]_r R$$
$$\underset{R^3}{\overset{|}{(OCHCH_2)_e}}OCH_2-\underset{C_2H_4R^2}{\overset{|}{CHR^1}}$$

wherein $R^1$ and $R^2$ are each independently alkyl or alkenyl having from 5 to 25 carbon atoms; $R^3$ is hydrogen, methyl or ethyl; d and e each have a value of from 0 to 150; r has a value of from 2 to 4 and, when r is 2, R is selected from the group of

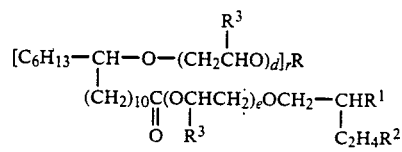

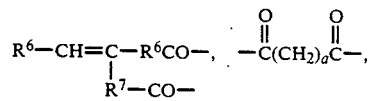

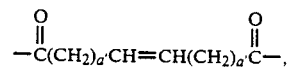

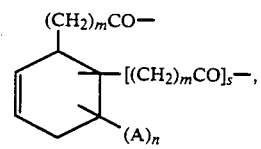

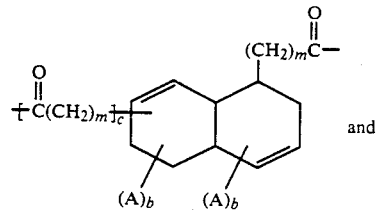

and

-continued

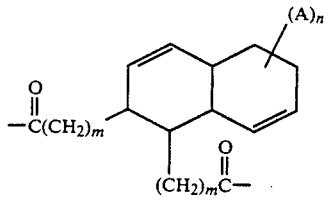

wherein m has a value of from 1 to 10; n has a value of from 0 to 2, each of b and c have a value of from 0 to 1; s s has a value of from 1 to 3 and the sum of s+n is from 1 to 3; each $R^6$ is alkyl; $R^7$ is alkylene; A is alkyl, alkenyl or a mixture thereof; a has a value of from 1 to 36 and a' has a value of from 0 to 36, and when r has a value greater than 2, R is

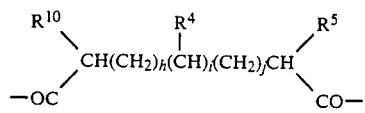

where each of h, i and j have a value of from 0 to 12, and $R^{10}$, $R^4$ and $R^5$ are each hydrogen or —CO— or —COOH, with the proviso that at least one of $R^{10}$, $R^4$ and $R^5$ is —CO—.

Species of R when r is 2, include the divalent radicals:

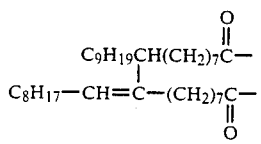

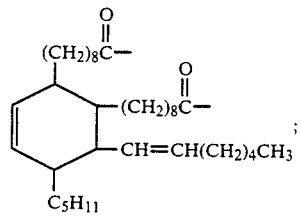

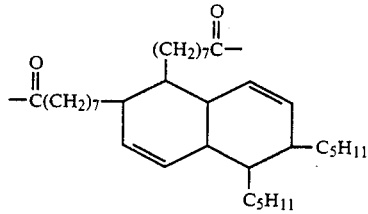

Of the above group of compounds, those wherein d and e each have a value of from 0 to 15; $R^1$ and $R^2$ are each independently alkyl or alkenyl having from 12 to 20 carbon atoms and R is

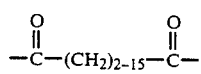

or

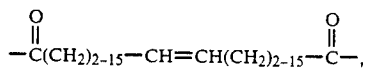

are preferred and those wherein a and a' have a value of from 4 to 12 are most preferred.

Suitable diacids which can be employed in the present process include oxalic, adipic, succinic, melonic, glutaric, pimelic, suberic, sebacic, maleic, azelic, dodecanedioic, fumaric and dimer acids, such as those described in U.S. Pat. Nos. 2,482,761; 2,793,219; 2,793,220; 2,955,121; 3,076,003 and 3,100,784, incorporated herein by reference. Examples of such dimer acids are the mixtures of acyclic, monocyclic and bicyclic species such as those conforming to the structure

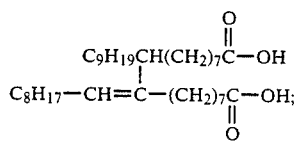

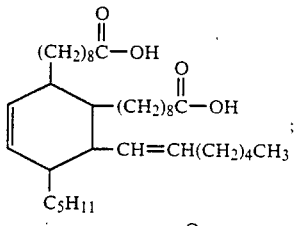

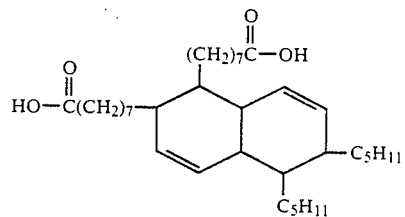

Examples of tri- and tetra- dicarboxylic acids include aconitic, tricarboxylic octanoic acid, tricarballylic acid, tetracarboxylic decanoic acid, octadecyl tetracarboxylic acid, dodecyl tricarboxylic acid, ethane tetracarboxylic acid, butane tetracarboxylic acid, etc.

The guerbet alcohols formed from a single alcohol are those wherein $R^1$ and $R^2$ are identical and are termed "homo- guerbet alcohols". However, when the guerbet alcohol is the reaction product of different linear alcohols, $R^1$ and $R^2$ in the resulting product are disimilar and are termed "hetero- guerbet alcohols". Either of these types are suitably employed as reactants in the synthesis of the present compounds and, because of their terminal position in the product, are particularly important to lend clarity to the polycarbonate resins with which the product is combined. Such resins have a high requirement for clarity as they are often used to form optical articles of manufacture. Particularly preferred guerbet alcohol reactants are those having the formula

wherein d is as defined above and R" is alkyl having from 10 to 18 carbon atoms. The lower alkyl carboxylates of these acids are also usefully employed.

Representative of the reactions for synthesizing the products of this invention, where r has a value of 2, are illustrated by method I in equations A-D and Method II in equations E and F.

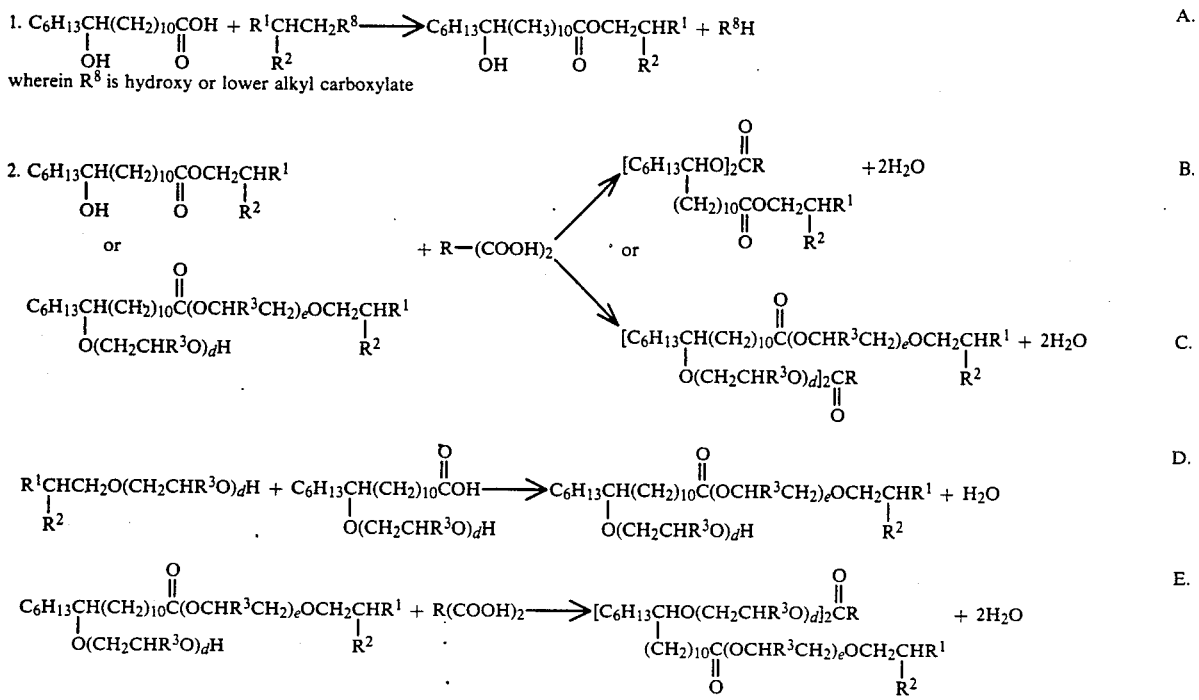

wherein d, e, R, $R^1$, $R^2$ and $R^3$ are as defined.

The products A and B are described in more detail in applicant's copending patent application Ser. No. 139,322, filed on Dec. 30, 1987 and entitled HYDROXY STEARIC ESTERS, the disclosure of which is incorporated herein by reference.

For simplification in the above methods, dicarboxylic acid is shown for steps B, C and E; however, it is within the scope of this invention to employ tri- and tetra-carboxylic acids where 3 and 4 units of the products shown in step C and E are bonded to the R moiety. Synthesis methods for preparing the tri- or tetracarboxylic acid derivatives are substantially similar to those employed for the above reactions.

The broad and preferred conditions for reactions A, B, C, D and E are tabulated below in Table I.

TABLE I

| | Reaction Time (hrs.) Broad/Preferred | Reaction Temp. (°C.) Broad/Preferred | Reaction Pressure (mm Hg) Broad/Preferred |
|---|---|---|---|
| Reaction | | | |
| A | 2–20/8–10 | 140–240/180–210 | 5–760/20–760 |
| B | 2–20/8–10 | 140–240/180–210 | 5–760/20–760 |
| C | 2–20/8–10 | 140–240/180–210 | 5–760/20–760 |
| D | 2–20/8–10 | 140–240/180–210 | 5–760/20–760 |
| E | 2–20/8–10 | 140–240/180–210 | 5–760/20–760 |

The esterification reactions of A and D are preferably carried out in the presence of a catalyst which is employed at a concentration of between about 0.05 and about 0.5% by weight, preferably within the range of from about 0.1% to about 0.3% by weight. Effective esterification catalysts which can be employed include sulfuric acid, p-toluene sulfonic acid, methane sulfonic acid, metallic tin, metallic zinc, metallic titanium, organotitianates, organo tin compounds, organo zinc compounds, zinc oxide, magnesium oxide, calcium oxide and stannous oxylate. The esterification is beneficially conducted under a blanket of nitrogen and water is removed during the reaction by using a nitrogen sparge or a vacuum of up to 10 mm Hg.

The thermoplastic resins which are benefited by inclusion of the present guerbet derived lubricants include resins of polystyrene, polyvinyl chloride, polyphenylene oxide, styrene-acrylonitrile copolymer (SAN), polysulfones, polyarylates, polyamides, polyimides, polyesters, butadiene rubber modified SAN (ABS), ethylene-propylene-diene rubber modified SAN (AES), polycarbonate, polyester carbonates and the like including mixtures and polymeric amalgams thereof; polycarbonate thermoplastic resins being preferred.

The polycarbonates with which the present esters are particularly effective lubricants include homopolycarbonates and copolycarbonates which are based, for example, on one or more of the following bisphenols: hydroquinone, resorcinol, dihydroxydiphenyls, bis-(hydroxyphenyl)-alkanes, bis-(hydroxyphenyl)-cycloalkanes, bis-(hydroxyphenyl)-sulfides, bis-(hydroxyphenyl)-ethers, bis-(hydroxyphenyl)-ketones, bis-(hydroxyphenyl)-sulfoxides, bis-(hydroxyphenyl)-sulfones and α, α-bis(hydroxyphenyl)-diisopropyl-benzenes, as well as their nuclear alkylated and nuclear-halogenated compounds. These and other suitable aromatic dihydroxy compounds are described, for example, in U.S. Pat. Nos. 3,028,365, 2,999,835, 3,148,172, 3,271,368, 2,991,273, 3,271,367, 3,280,078, 3,014,891 and 2,999,846 and are incorporated herein by reference.

Among the various types of polycarbonates, those derived from the reaction of phosgene or the transesterification of diphenyl carbonate with diphenolic compounds of the following formula are preferred.

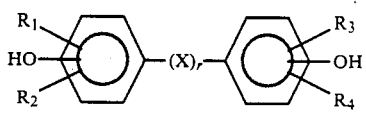

where $R_1$, $R_2$, $R_3$ and $R_4$ are each independently hydrogen, lower alkyl or halogen; r has a value of 0 or 1 and X is —SO—;

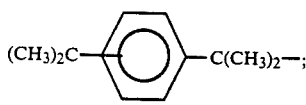

alkylene; alkylidene; phenyl substituted alkylene or phenyl substituted alkylidene; cycloalkylene, monoalkyl- or polyalkyl-phenylene; cycloalkylidene, or ether, thioether, ketone, sulfone or sulfoxide containing derivatives thereof, having up to 30 carbons. Examples of these preferred thermoplastic polycarbonates include those prepared from 4,4'-isopropylidene diphenol (bisphenol A), 4,4'-dihydroxydiphenyl, 1,1-bis(4-hydroxyphenyl)-1-phenylethane, 2,4-bis(4-hydroxyphenyl)-2-methyl butane, 1,1-bis(4-hydroxyphenyl)-cyclohexane 2,3-bis(4-hydroxyphenyl)-sulfoxide, 2,2-bis(3-methyl-4-hydroxyphenyl)-propane 2,4-bis(3-chloro-4-hydroxyphenyl)-butane 2,4-bis(4-hydroxyphenyl)2-butene 2,3-bis(3,5-dimethyl-4-hydroxyphenyl)-propane 2,3-bis(3,5-diethyl-4-hydroxyphenyl)-2-methylbutane 2,2-bis(3,5-dichloro-4-hydroxyphenyl)-propane 2,2-bis(3,5-dibromo-4-hydroxyphenyl)-propane. A highly preferred polycarbonate is bisphenol A polycarbonate.

Examples of particularly preferred bisphenols are: 2,2-bis-(4-hydroxyphenyl)-propane, 2,2-bis-(3,5-dimethyl-4-hydroxyphenyl)-propane, 2,2-bis-(3,5-dichloro-4-hydroxyphenyl)-propane, 2,2-bis-(3,5-dibromo-4-hydroxyphenyl)-propane, and 1,1-bis-(4-hydroxyphenyl)-cyclohexane.

Particularly preferred copolycarbonates are those based on 2,2-bis-(4-hydroxyphenyl)-propane and one of the other bisphenols mentioned. Further particularly preferred polycarbonates are those based solely on 2,2-bis-(4-hydroxyphenyl)-propane or 2,2-bis-(3,5-dimethyl-4-hydroxyphenyl)-propane.

The aromatic polycarbonates can be branched due to the incorporation of small amounts, preferably of between 0.05 and 2.0 mol % (relative to diphenols employed), of polyfunctional compounds, especially compounds with three or more phenolic hydroxyl groups. Polycarbonates of this type are described, for example, in German Offenlegungsschriften (German Published Specifications) Nos. 1,570,533, 1,595,762, 2,116,974 and 2,113,347; British Patent Specification No. 1,079,821; U.S. Pat. No. 3,544,514 and German Patent Application No. P 25 00 092.4.

Some examples of compounds with three or more phenolic hydroxyl groups which can be used are: phloroglucinol, 4,6-dimethyl-2,4,6-tri-4-hydroxyphenyl)-heptane-2, 4,6-dimethyl-2,4,6-tri-(4-hydroxyphenyl)-heptane, 1,4,5-tri-(4-hydroxyphenyl)-benzene, 1,1,1-tri-(4-hydroxyphenyl)-ethane, tri-(4-hydroxyphenyl)-phenylmethane, 2,2-bis-(4,4-bis-(4-hydroxyphenyl)-cyclohexyl)-propane, 2,4-bis-(4-hydroxyphenylisopropyl)-phenol, 2,6-bis-(2-hydroxy-5-methylbenzyl)-4-methylphenol, 2-(4-hydroxyphenol), 2-2,4-(dihydroxyphenyl)-propane, hexa(4-(4-hydroxyphenylisopropyl)-phenyl)orthoterephthalic acid ester, tetra-(4-hydroxyphenyl)-methane and 1,4-bis-((4',4''-dihydroxytriphenyl)methyl)-benzene. Other polyfunctional compounds include 2,4-dihydroxybenzoic acid and trimesic acid.

The thermoplastic polymers employed in the present compositions preferably have a mean weight average molecular weight of from about 10,000 to 3 million. Polycarbonates employed in the present compositions preferably have a mean weight-average molecular weight of from about 10,000 to about 200,000; most preferably from about 20,000 to about 80,000; (as determined by measurement of relative viscosity in $CH_2Cl_2$ at 25° C. at a concentration of 0.5% by weight using a polystyrene standard).

The thermoplastic polymer or mixture of thermoplastic polymers are mixed in particulate form with the present lubricant or the polymer or mixture of polymers can be combined as a melt with the lubricant.

The branched guerbet alcohol derived esters are preferably employed in a concentration of from about 0.025% to about 1.0%; most preferably from about 0.1% to about 0.25% by weight of the total thermoplastic resin compositions. However, concentrations of from about 0.01% to about 2% by weight can be employed, if desired.

In general the additives may be added to the polymer prior to devolatilization, or at any time prior to or during any extrusion or molding operation so as to obtain uniform incorporation and dispersion thereof. In a highly preferred embodiment there is provided a particulated thermoplastic resin product comprising a surface coating of a lubricating quantity of the above branched guerbet alcohol derived esters. Such particulated polymeric products have been found to possess improved solid handling properties, most notably reduced feed times to an extruder, faster melting and feed rates to the extruder and less entrained air into the polymer melt due to smoother feed and melting properties.

The present compositions also possess improved melt flow characteristics and mold release properties. This is particularly advantageous in polycarbonate containing formulations, in that the use of higher molecular weight resins in standard molding or extrusion equipment is possible.

The thermoplastic polycarbonate compositions, using the lubricants of the present invention, find use in several high performance areas. Such examples of use for the polycarbonates of the present invention utilizing the lubricant agents include laser read compact recording discs, precision extrusion of polycarbonate sheets for use in greenhouses and in products safe for food contact like water and other beverage bottles, microwave wear, baby formula bottles, beer mugs, pitchers, and food storage containers and other similar high performance specialty applications.

The thermoplastic resin containing composition is preferably molded or extruded into facia or sheets at a temperature of between 200° C. and 400° C. under a pressure of from about 2,000 to about 30,000 psi; preferably at a temperature of between 260° C. and 380° C. under a pressure of from about 5,000 to about 20,000 psi; and most preferably between 280° C. and 350° C. The molded or extruded product is then cooled to room temperature. Other thermoplastic resins can be shaped at different temperatures, depending on their glass transition temperatures. The product can be recovered as a particulated thermoplastic polymeric product comprising a surface coating of a lubricating quantity of the present guerbet derived branched ester compound.

Additional additives and modifying components of conventional design may be incorporated into the compositions of the invention if desired. For example thermal stabilizers or antioxidants such as phosphates, phosphonates or thiophosphates; ignition resistant additives including sulfur compounds, halogenated compounds, salts and polytetrafluoroethylene; fibrous reinforcing additives, including glass, boron or graphite fibers; fillers, such as mica, talc, clays, etc., rubbery impact modifiers, such as butadiene based elastomers, acrylates, saturated rubbers and polar copolymer grafted derivatives thereof may be incorporated into the present compositions without departing from the scope of the present invention.

Although lacking many of the benefits and advantages of incorporating the present guerbet derived branched ester in a composition including the thermoplastic resin, the present resins could also be sprayed on the inner surface of a mold as a mold release agent. In this capacity the ester can be employed for molds shaping larger facia where release in a matter of seconds is not required, e.g. in forming automotive facia. In this case guerbet derived esters can be used in an unadulterated state or they can be diluted or emulsified with an inert solvent or emulsifying agent.

Having thus described the invention, reference is now had to the following examples which illustrate preferred embodiments and comparative examples but which are not to be construed as limiting to the scope of the invention as more broadly set forth above and in the appended claims.

EXAMPLE 1 *

Into a glass reaction vessel attached to a distillation column was added with constant agitation 488.0 grams of the alkoxylated guerbet alcohol of the formula

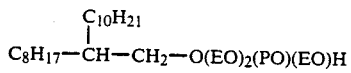

PO in the Examples is intended to be

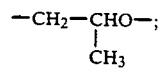

OE is —OCH$_2$CH$_2$ and, OP is

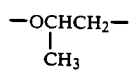

and 346.0 grams of the acid having the formula

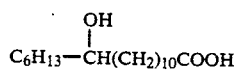

under a nitrogen sparge. To this mixture was added 2.0 grams of para toluene sulfonic acid (esterification catalyst) and the reaction mixture was gradually heated to 200° C. During reaction, water was distilled off and vacuum was applied as the rate of distillation slowed. A minimum total of 97% of the theoretical water was removed. After the removal of water 73.0 grams of adipic acid was added to the reactor and the reaction was continued at 140°–200° C. during which time additional quantities of water were removed by distillation and application of vacuum as above, until a minimum of 97% of the theoretical water was drawn off. The product,

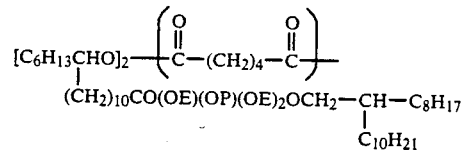

was recovered in 92% yield.

EXAMPLE 2

Into a glass reaction vessel attached to a distillation column was added with constant agitation 388.0 grams of the alkoxylated guerbet alcohol of the formula

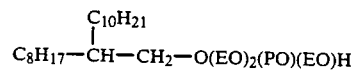

and 346.0 grams of the acid having the formula

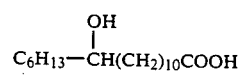

under a nitrogen sparge. To this mixture was added 2.0 grams of para toluene sulfonic acid (esterification catalyst) and the reaction mixture was gradually heated to 200° C. During reaction, water was distilled off and vacuum was applied as the rate of distillation slowed. A minimum total of 97% of the theoretical water was removed. After the removal of water 115 grams of dodecanedioic acid was added to the reactor and the reaction was continued at 140°–200° C. during which time additional quantities of water were removed by distillation and application of vacuum as above, until a minimum of 97% of the theoretical water was drawn off. The product

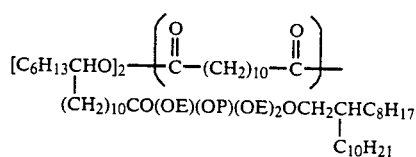

was recovered in 93% yield.

EXAMPLE 3

Into a glass reaction vessel attached to a distillation column was added with constant agitation 225 grams of the guerbet alcohol of the formula

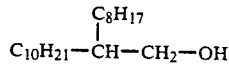

and 449 grams of the acid having the formula

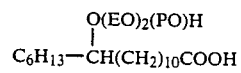

under a nitrogen sparge. To this mixture was added 2.0 grams of an organic titanate esterification catalyst and the reaction mixture was gradually heated to 200° C. During reaction, water was distilled off and vacuum was applied as the rate of distillation slowed. A minimum total of 97% of the theoretical water was removed. After the removal of water 211.9 grams of maleic acid was added to the reactor and the reaction was continued at 140°-200° C. during which time additional quantities of water were removed by distillation and application of vacuum as above, until a minimum of 97% of the theoretical water was drawn off. The product,

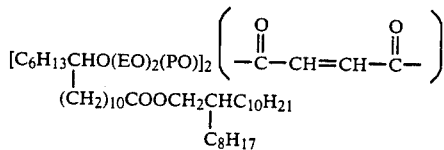

was recovered in 90% yield.

EXAMPLE 4

Into a glass reaction vessel attached to a distillation column was added with constant agitation 225 grams of the guerbet alcohol of the formula

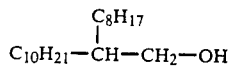

and 449 grams of the acid having the formula

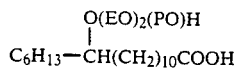

under a nitrogen sparge. To this mixture was added 2.0 grams of para toluene sulfonic acid (esterification catalyst) and the reaction mixture was gradually heated to 200° C. During reaction, water was distilled off and vacuum was applied as the rate of distillation slowed. A minimum total of 97% of the theoretical water was removed. After the removal of water 145 grams of dimer acid, Empol 1024* was added to the reactor and the reaction was continued at 140°-200° C. during which time additional quantities of water were removed by distillation and application of vacuum as above, until a minimum of 97% of the theoretical water was drawn off.
* HOOCC$_{34}$H$_{64}$—COOH The product

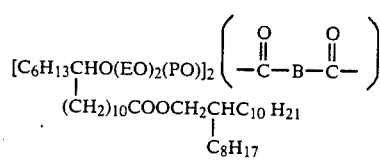

wherein B is a mixture of

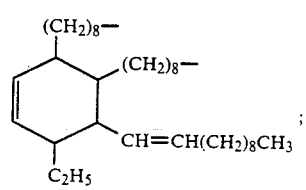

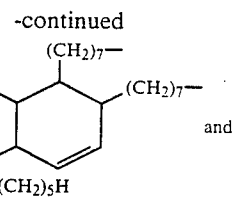

and

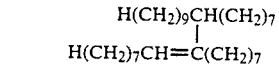

was recovered in 95% yield.

EXAMPLE 5

Into a glass reaction vessel attached to a distillation column was added with constant agitation 372 grams of the alkoxylated guerbet alcohol of the formula

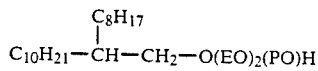

and 449 grams of the acid having the formula

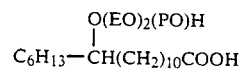

under a nitrogen sparge. To this mixture was added 2.0 grams of para toluene sulfonic acid (esterification catalyst) and the reaction mixture was gradually heated to 200° C. During reaction, water was distilled off and vacuum was applied as the rate of distillation slowed. A minimum total of 97% of the theoretical water was removed. After the removal of water 136 grams of azelaic acid was added to the reactor and the reaction was continued at 140°-200° C. during which time additional quantities of water were removed by distillation and application of vacuum as above, until a minimum of 97% of the theoretical water was drawn off. The product,

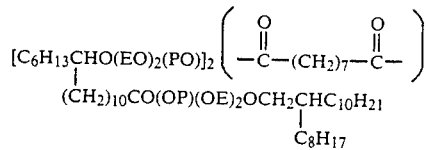

was recovered in 92% yield.

EXAMPLE 6

Into a glass reaction vessel attached to a distillation column was added with constant agitation 416 grams of the alkoxylated guerbet alcohol of the formula

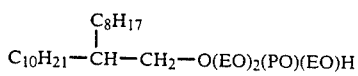

and 449 grams of the acid having the formula

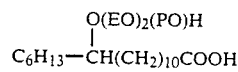

under a nitrogen sparge. To this mixture was added 2.0 grams of tin oxide esterification catalyst and the reaction mixture was gradually heated to 200° C. During reaction, water was distilled off and vacuum was applied as the rate of distillation slowed. A minimum total of 97% of the theoretical water was removed. After the removal of water 59 grams of succinic acid was added to the reactor and the reaction was continued at 140°-200° C. during which time additional quantities of water were removed by distillation and application of vacuum as above, until a minimum of 97% of the theoretical water was drawn off. The product,

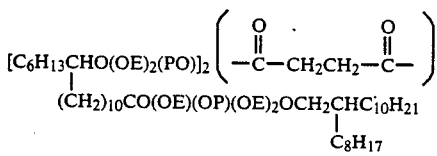

was recovered in 94% yield.

EXAMPLE 7

Into a glass reaction vessel attached to a distillation column was added with constant agitation 197 grams of the guerbet alcohol of the formula

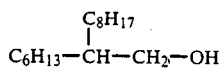

and 449 grams of the acid having the formula

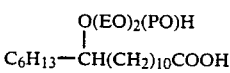

under a nitrogen sparge. To this mixture was added 2.0 grams of para toluene sulfonic acid (esterification catalyst) and the reaction mixture was gradually heated to 200° C. During reaction, water was distilled off and vacuum was applied as the rate of distillation slowed. A minimum total of 97% of the theoretical water was removed. After the removal of water 73.0 grams of adipic acid was added to the reactor and the reaction was continued at 140°-200° C. during which time additional quantities of water were removed by distillation and application of vacuum as above, until a minimum of 97% of the theoretical water was drawn off. The product,

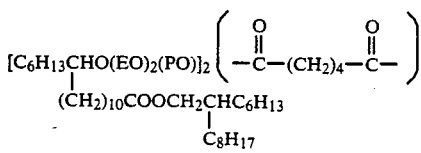

was recovered in 92% yield.

EXAMPLE 8

Into a glass reaction vessel attached to a distillation column was added with constant agitation 241 grams of the alkoxylated guerbet alcohol of the formula

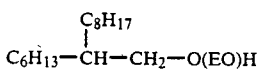

and 346.0 grams of the acid having the formula

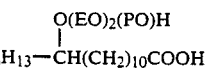

under a nitrogen sparge. To this mixture was added 2.0 grams of para toluene sulfonic acid (esterification catalyst) and the reaction mixture was gradually heated to 200° C. During reaction, water was distilled off and vacuum was applied as the rate of distillation slowed. A minimum total of 97% of the theoretical water was removed. After the removal of water 73.0 grams of adipic acid was added to the reactor and the reaction was continued at 140°-200° C. during which time additional quantities of water were removed by distillation and application of vacuum as above, until a minimum of 97% of the theoretical water was drawn off. The product,

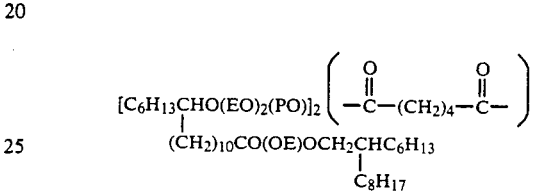

was recovered in 96% yield.

EXAMPLE 9

Into a glass reaction vessel attached to a distillation column was added with constant agitation 388 grams of the alkoxylated guerbet alcohol of the formula

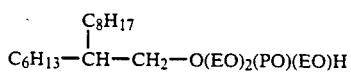

and 449 grams of the acid having the formula

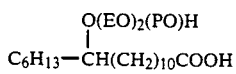

under a nitrogen sparge. To this mixture was added 2.0 grams of para toluene sulfonic acid (esterification catalyst) and the reaction mixture was gradually heated to 200° C. During reaction, water was distilled off and vacuum was applied as the rate of distillation slowed. A minimum total of 97% of the theoretical water was removed. After the removal of water 145 grams of dimer acid (Empol 1024) was added to the reactor and the reaction was continued at 140°-200° C. during which time additional quantities of water were removed by distillation and application of vacuum as above, until a minimum of 97% of the theoretical water was drawn off. The product,

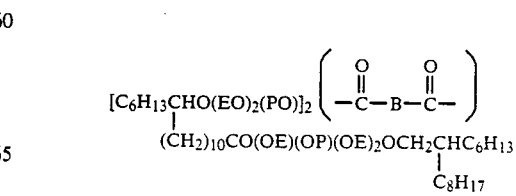

wherein B is a mixture of

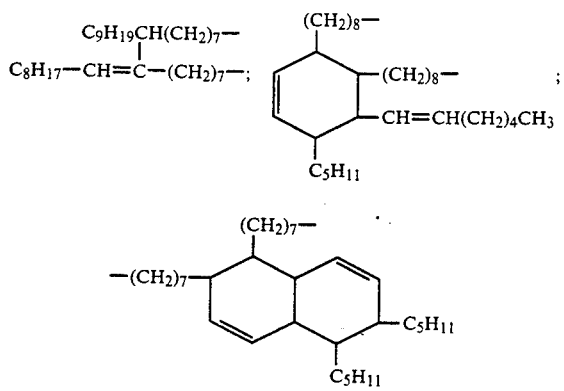

was recovered in 96% yield.

EXAMPLE 10

Into a glass reaction vessel attached to a distillation column was added with constant agitation 388 grams of the alkoxylated guerbet alcohol of the formula

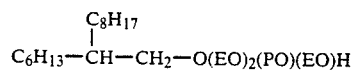

and 449 grams of the acid having the formula

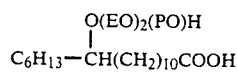

under a nitrogen sparge. To this mixture was added 2.0 grams of para toluene sulfonic acid (esterification catalyst) and the reaction mixture was gradually heated to 200° C. During reaction, water was distilled off and vacuum was applied as the rate of distillation slowed. A minimum total of 97% of the theoretical water was removed. After the removal of water 58 grams of maleic acid was added to the reactor and the reaction was continued at 140°-200° C. during which time additional quantities of water were removed by distillation and application of vacuum as above, until a minimum of 97% of the theoretical water was drawn off. The product,

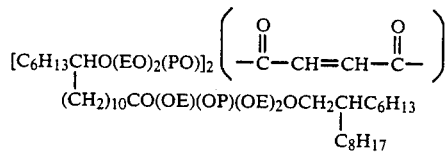

was recovered in 92% yield.

EXAMPLE 11

Into a glass reaction vessel attached to a distillation column was added with constant agitation 225 grams of the guerbet alcohol of the formula

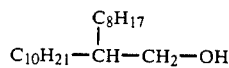

and 493 grams of the acid having the formula

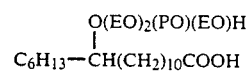

under a nitrogen sparge. To this mixture was added 2.0 grams of tin oxide esterification catalyst and the reaction mixture was gradually heated to 200° C. During reaction, water was distilled off and vacuum was applied as the rate of distillation slowed. A minimum total of 97% of the theoretical water was removed. After the removal of water 136 grams of azelaic acid was added to the reactor and the reaction was continued at 140°-200° C. during which time additional quantities of water were removed by distillation and application of vacuum as above, until a minimum of 97% of the theoretical water was drawn off. The product,

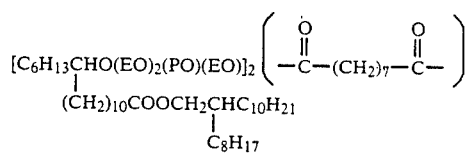

was recovered in 94% yield.

EXAMPLE 12

Into a glass reaction vessel attached to a distillation column was added with constant agitation 225 grams of the guerbet alcohol of the formula

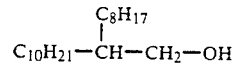

and 493 grams of the acid having the formula

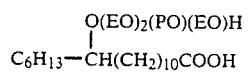

under a nitrogen sparge. To this mixture was added 2.0 grams of para toluene sulfonic acid (esterification catalyst) and the reaction mixture was gradually heated to 200° C. During reaction, water was distilled off and vacuum was applied as the rate of distillation slowed. A minimum total of 97% of the theoretical water was removed. After the removal of water 52 grams of malonic acid was added to the reactor and the reaction was continued at 140°-200° C. during which time additional quantities of water were removed by distillation and application of vacuum as above, until a minimum of 97% of the theoretical water was drawn off. The product,

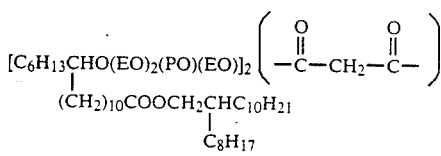

was recovered in 96% yield.

EXAMPLE 13

Into a glass reaction vessel attached to a distillation column was added with constant agitation 372 grams of the alkoxylated guerbet alcohol of the formula

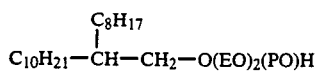

and 493 grams of the acid having the formula

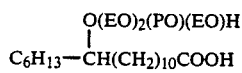

under a nitrogen sparge. To this mixture was added 2.0 grams of stannous oxylate esterification catalyst and the reaction mixture was gradually heated to 200° C. During reaction, water was distilled off and vacuum was applied as the rate of distillation slowed. A minimum total of 97% of the theoretical water was removed. After the removal of water 52 grams of malonic acid was added to the reactor and the reaction was continued at 140°-200° C. during which time additional quantities of water were removed by distillation and application of vacuum as above, until a minimum of 97% of the theoretical water was drawn off. The product,

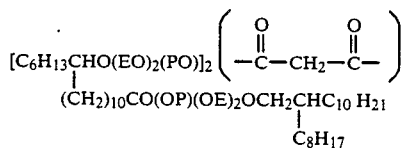

was recovered in 96% yield.

EXAMPLE 14

A polycarbonate bisphenol, LEXAN 181, supplied by General Electric, was mixed with 0.5 wt. % of the product of Example 3. The mixture was then melted and extruded through a twin screw extruder at a temperature of 300° C. under 15,000 psi. The resulting product was evaluated for clarity and for the presence of lubricating agent on the surface of the polycarbonate extruded sheet. For determining migration of lubricant to the surface of the polycarbonate, an isopropanol washing procedure was employed. This procedure was carried out by immersing a 100 gram, ⅛ inch thick sample of the extruded polycarbonate sheet in 400 ml of isopropanol for a period of 8 hours. The sample was then removed and the alcohol transferred to a preweighed distillation flask. The isopropanol was distilled off and the flask was heated at 100° C. in an oven overnight and then cooled in a desiccator. The residue remaining in the flask represents the amount of lubricant which migrated to the surface of the polycarbonate sample.

In the present case, the polycarbonate sheet was uniformly clear and no residue remained in the distillation flask, indicating that there was no migration of lubricant to the surface of the polycarbonate sample.

The above procedure was repeated using each of the compounds of Examples 1 and 2 substituted for the compound of Example 3 In each case, the polycarbonate sheet remained uniformly clear and no residue remained in the distillation flask except in the case of Example 1 where a 10 milligram residue was recovered as a clear liquid.

For comparison Example 1 was repeated with the commercial internal lubricant, pentaerythritol tetrastearate. In this case, a residue of 128 milligrams was recovered as a yellowish powder and the extruded polycarbonate sheet containing the lubricant showed definite yellowing.

EXAMPLE 15

Into a glass reaction vessel attached to a distillation column is added with constant agitation 300 grams of the guerbet alcohol of the formula

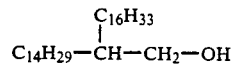

and 594 grams of the acid having the formula

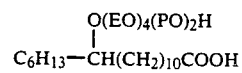

under a nitrogen sparge. To this mixture is added 2.0 grams of para toluene sulfonic acid esterification catalyst and the reaction mixture is gradually heated to 200° C. During reaction, water is distilled off and vacuum is applied as the rate of distillation slowed. A minimum total of 97% of the theoretical water is removed. After the removal of water 32 grams of ethane tetracarboxylic acid is added to the reactor and the reaction is continued at 140°-200° C. during which time additional quantities of water are removed by distillation and application of vacuum as above, until a minimum of 97% of the theoretical water is drawn off. The product,

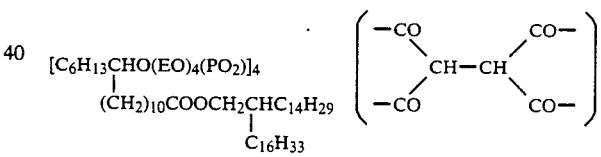

is recovered in good yield.

EXAMPLE 16

Into a glass reaction vessel attached to a distillation column is added with constant agitation 670 grams of the alkoxylated guerbet alcohol of the formula

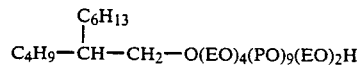

and 449 grams of the acid having the formula

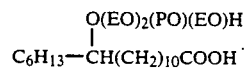

under a nitrogen sparge. To this mixture is added 2.0 grams of para toluene sulfonic acid esterification catalyst and the reaction mixture is gradually heated to 200° C. During reaction, water is distilled off and vacuum is applied as the rate of distillation slowed. A minimum total of 97% of the theoretical water is removed. After the removal of water 57.6 grams of propane-1,2,3-tricarboxylic acid was added to the reactor and the reaction is continued at 140°–200° C. during which time additional quantities of water are removed by distillation and application of vacuum as above, until a minimum of 97% of the theoretical water was drawn off. The product,

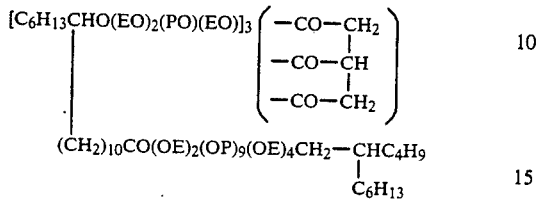

is recovered in good yield.

It will be understood that many alterations and substitutions can be made in the above examples without departing from the scope of this invention.

For example, any of the polyesters described above wherein R is other than an alkylene group can be substituted in the examples to provide uniformly clear polycarbonate samples with little or no migration to the surface of the polycarbonate with which they are intimately intermixed. It is also to be understood that the extrusion or molding of the foregoing types of polycarbonate in admixture with the products of this invention can be carried out at a temperature within the range of between about 280° and 350° C. under pressures of from about 5,000 to about 20,000 psig. Other molding techniques can also be employed. Further modifications of the foregoing procedures, which are also included within the scope of this invention, will become apparent to those skilled in the art.

Having thus described the invention,

What is claimed is:

1. A branched polyester having the formula

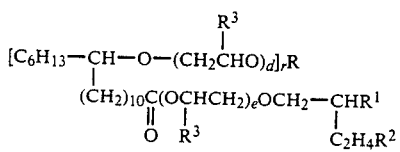

wherein $R^1$ and $R^2$ are each independently alkyl or alkenyl having from 5 to 25 carbon atoms; $R^3$ is hydrogen methyl or ethyl; d and e each have a value of from 0 to 150; r has a value of from 2 to 4 and, when r is 2, R is selected from the group of

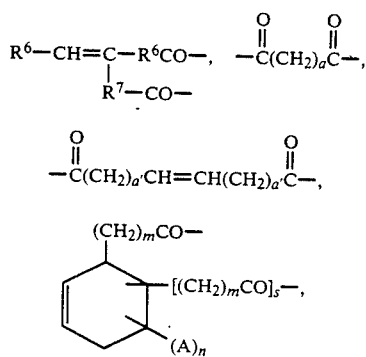

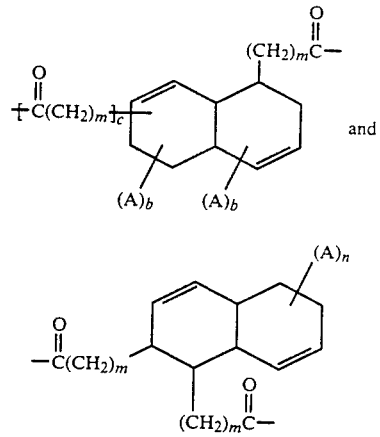

wherein A is alkyl, alkenyl or a mixture f; m has a value of from 1 to 10; n has a value of from 0 to 2; each of b and c has a value of 0 or 1; s has a value of from 1 to 3 and the sum of s+n is from 1 to 3; each $R^6$ is alkyl; $R^7$ is alkylene; a has a value of from 1 to 36 and a' has a value of from 0 to 36, and when r has a value greater than 2, R is

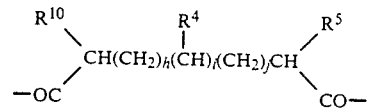

where each of h, i and j have a value of from 0 to 12, and $R^{10}$, $R^4$ and $R^5$ can be hydrogen, —COOH or —CO—, except that one of $R^{10}$, $R^4$ and $R^5$ is —CO— when r is 3 and two of $R^{10}$, $R^4$ and $R^5$ are —CO— when r is 4.

2. The polyester of claim 1 wherein d and e each have a value of from 0 to 15, and $R^1$ and $R^2$ are each independently alkyl or alkenyl having from 12 to 20 carbon atoms.

3. The polyester of claim 2 wherein r has a value of 2 and R is —CO(CH$_2$)$_{2-15}$—CO— or —CO(CH$_2$)$_{2-15}$—CH=CH—(CH$_2$)$_{2-15}$—CO—.

4. The polyester of claim 3 wherein R is —CO(CH$_2$)$_{4-12}$—CO— or —CO(CH$_2$)$_{4-12}$—CH=CH—(CH$_2$)$_{4-12}$—CO—.

5. The polyester of claim 2 wherein r has a value of 3 to 4 and R is

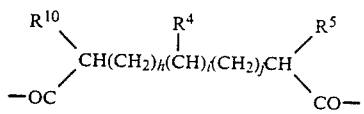

where h, i and j have a value of from 0 to 12, and at least one of $R^{10}$, $R^4$ and $R^5$ is hydrogen or —COOH the remaining being —CO—.

6. The polyester of claim 2 wherein d and e are each zero.

7. The polyester of claim 1 wherein d is zero and e is a positive integer.

8. The polyester of claim 1 wherein e is zero and d is a positive integer.

9. The process for synthesizing the polyester of claim 1 which comprises (a) contacting a reactant having the formula

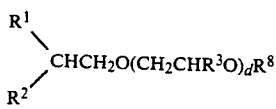

where $R^8$ is —OH or —OCO(lower alkyl) with an acid having the formula

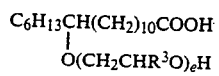

and reacting said compounds at a temperature of between about 140° and about 250° C. under from about 5 mm Hg to about 760 mm Hg for a period of from about 2 to about 20 hours to form an ester intermediate and (b) reacting said ester intermediate with a polycarboxylic acid having a formula selected from the group consisting of

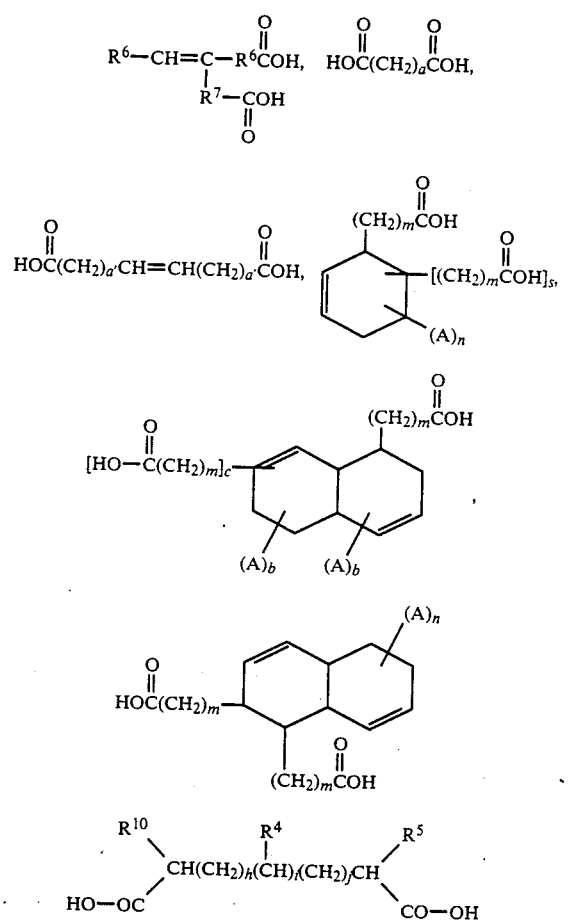

at a temperature of between about 140° and about 240° C. under a pressure of from about 5 mm Hg to about 760 mm Hg for a period of from about 2 to about 10 hours wherein $R^8$ is hydrogen or —OCO (lower alkyl) and $R^4$, $R^5$, and $R^{10}$ are each hydrogen, —CO— or —COOH and wherein A, $R^1$, $R^2$, $R^3$, $R^4$, $R^5$, $R^6$, $R^7$, $R^{10}$, a, a', b, c, d, e, h, i, j, m, n, and s are as defined in claim 1.

10. The process of claim 9 wherein water by-product is removed during process steps (a) and (b).

11. The process of claim 10 wherein d is zero.

12. The process of claim 10 wherein step (a) is effected in the presence of between about 0.05% and about 0.5% by weight of an esterification catalyst.

13. the process of claim 9 wherein said polycarboxylic acid is selected from the group of adipic, dodecanedioic, maleic, azelaic, succinic, malonic, ethane tetracarboxylic, propane tricarboxylic and dimer acids.

14. The process of claim 10 wherein at least 95% of water by-product is removed continuously during steps (a) and (b) of the process.

15. A polycarbonate resin composition containing an effective lubricating amount of the compound of claim 1.

16. The composition of claim 15 containing from about 0.025% to about 1.0% by weight of the compound of claim 1.

17. The composition of claim 15 wherein said polycarbonate is a polycarbonate homopolymer.

18. The composition of claim 15 wherein said polycarbonate is a polycarbonate copolymer.

19. The composition of claim 15 wherein said polycarbonate is a polycarbonate bis phenol having the formula

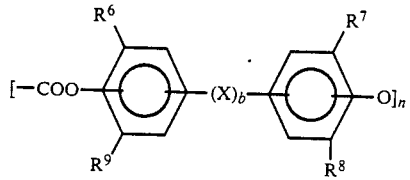

wherein n has a value of from about 400 to about 10,000; each of $R^6$, $R^7$, $R^8$ and $R^9$ is hydrogen, $C_1$ to $C_4$ alkyl, Cl or Br; b is 0 or 1 and X is $C_1$ to $C_8$ alkylene, $C_4$ to $C_{12}$ alkenylene, $C_5$ to $C_{15}$ cycloalkylene, $C_5$ to $C_{15}$ cycloalkenylene, —SO— or

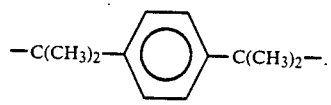

20. The composition of claim 19 wherein said polycarbonate is bis(hydroxyphenyl)-propane optionally substituted on the aromatic ring with lower alkyl.

* * * * *